United States Patent [19]

Takahashi

[11] 4,024,201
[45] May 17, 1977

[54] PROCESS FOR THE SELECTIVE DISPROPORTIONATION REACTION OF OLEFINS

[75] Inventor: Tadao Takahashi, Kawaguchi, Japan

[73] Assignee: Director-General of the Agency of Industrial Science and Technology, Tokyo, Japan

[22] Filed: Aug. 25, 1975

[21] Appl. No.: 607,703

[30] Foreign Application Priority Data

Aug. 26, 1974 Japan .............................. 49-97693
Sept. 6, 1974 Japan .............................. 49-103151
Dec. 7, 1974 Japan .............................. 49-141035

[52] U.S. Cl. ........................ 260/683 D; 260/683.2
[51] Int. Cl.² ........................................... C07C 3/62
[58] Field of Search .................... 260/683 D, 683.2

[56] References Cited

UNITED STATES PATENTS

| | | | |
|---|---|---|---|
| 2,816,905 | 12/1957 | Gilbert et al. | 260/683.2 |
| 3,544,647 | 12/1970 | Pennella | 260/683 |
| 3,546,311 | 12/1970 | Heckelsberg | 260/683 |
| 3,637,893 | 1/1972 | Singleton | 260/683 |
| 3,923,920 | 2/1975 | Regier | 260/683 |

*Primary Examiner*—C. Davis
*Attorney, Agent, or Firm*—William J. Daniel

[57] ABSTRACT

In the disproportionation reaction of a linear olefin such as 1-butene conducted in the presence of a supported tungsten oxide catalyst such as a tungsten oxide-silica catalyst, isomerization of the olefin is inhibited and the conversion ratio for the disproportionation reaction of the olefin is increased by conducting the reaction in the presence of an amine compound such as ammonia or n-butylamine or a halogen compound such as chloroform.

10 Claims, No Drawings

PROCESS FOR THE SELECTIVE DISPROPORTIONATION REACTION OF OLEFINS

BACKGROUND OF THE INVENTION

The present invention relates to a process for the selective disproportionation reaction of olefins wherein an amine or a halogen compound is caused to be present during the disproportionation reaction of an olefin conducted in the presence of a carried tungsten oxide catalyst, thereby inhibiting the isomerization reaction of the olefin and increasing the conversion ratio for the disproportionation of the olefin.

It is widely known that various linear olefins are modified, or in other words, subjected to the so-called disproportionation reaction on a catalyst such as a supported tungsten oxide catalyst or a supported molybdenum catalyst, thereby to form a mixture of olefins which are larger and smaller in the molecular weight than the original olefins. However, a number of solid catalysts capable of promoting the disproportionation reaction of olefins are also catalytically active for the isomerization reaction of olefins where the double bond of the olefins is transferred. Thus, it is usual that when such solid catalyst is used for the disproportionation reaction of olefins, the isomerization reaction also takes place concurrently with the desired disproportionation reaction. For example, the disproportionation reaction of 1-butene affords only a mixture of ethylene and cis- and trans-5-hexene. In the case of using a solid catalyst such as tungsten oxide-silica, however, cis- and trans-2-butene are also formed from 1-butene by virtue of the isomerization activity of the catalyst and the disproportionation reaction takes place between the 2-butene and 1-butene, thus resulting in the formation of propylene and cis- and trans-2-pentene. Similarly, 1- and 2-hexenes are formed from 3-hexene and 1-pentene is formed from 2-pentene. These products give higher disproportionation products and the end products eventually become a mixture of very complicate olefins.

The co-disproportionation reaction of 2-butene and isobutene gives isoamylene and propylene. However, isomerization of double bond is caused by the same catalyst also in this case and, as the result, 1-butene is formed from 2-butene. Thus, the co-disproportionation reaction of 2-butene and 1-butene also takes place and the above mentioned complicate disproportionation proceeds parallelly to the production of linear pentenes. As the separation of the linear pentenes from isoamylene is difficult, the formation of the linear pentenes poses a serious problem.

As a result of many studies made for overcoming the above drawbacks in the disproportionation reaction of olefins, it has now been found that when an amine and/or a halogen compound is allowed to be coexistent with a carried tungsten oxide catalyst, the isomerization reaction of olefins is inhibited and the desired disproportionation of olefins is attained efficiently. The present invention has been accomplished on the basis of the above finding.

BRIEF SUMMARY OF THE INVENTION

Accordingly, the present invention relates to a process for the disproportionation reaction of olefins which comprises subjecting an olefin to disproportionation in the presence of a supported tungsten oxide catalyst, characterized in that at least one compound selected from the group consisting of amines and halogen compounds is allowed to be coexistent with said catalyst.

It is an object of the present invention to provide a process for the disproportionation reaction of olefins wherein the rate of the desired disproportionation reaction of olefins is increased.

It is another object of the present invention to provide a process for the disproportionation reaction of olefins wherein the selectivity of the disproportionation reaction is improved.

Other and further objects, features and advantages of the invention will appear more fully from the following description.

DETAILED DESCRIPTION OF THE INVENTION

The compounds to be coexistent with the supported tungsten oxide catalyst for attaining the objects of the present invention are classified roughly into amines and halogen compounds.

Illustrative of the amines are ammonia, primary amines such as n-butylamine, isobutylamine, n-propylamine and ethylamine; secondary amines such as diethylamine; tertiary amines such as triethylamine; and cyclic amines such as piperidine. Although the activity to isomerization of the catalyst is poisoned by the existence of these amines, the activity to disproportionation of the catalyst is rather enhanced. In the case of using piperidine, not only the activity to isomerization but also that to disproportionation are poisoned. In this case, however, lowering of the former is extremely remarkable as compared with the latter. Accordingly, the use of piperidine serves as a whole to improve the selectivity.

The halogen compounds useful for the present invention include chlorine compounds such as chloroform and carbon tetrachloride as well as bromine compounds such as dibromomethane, 1,1-dibromoethane and n-butyl bromide.

The amount of the amine and/or the halogen compound used varies according to the reaction temperature, the sort of starting materials and the sort of compounds to be added, but is usually within a range of 0.001–5 mol % based on the starting olefin. Preferably, the amount is within a range of 0.5–2.0 mol % (in the case of ammonia) and within a range of 0.01–0.5 mol % (in the case of halogen compounds or amine compounds other than ammonia) based on the olefin.

As a means for adding such amine and/or halogen compound to the reaction system, the compound may be allowed to be present originally together with the catalyst or intermittently injected as pulse during the reaction or passed continuously through the catalyst later. In a test according to the pulse method, n-butylamine or isobutylamine temporarily enhances the activity to disproportionation and at the same time lowers the activity to isomerization, but after the lapse of a certain period of time the effect of the above amine is reversed. In case such amine is introduced continuously into the reaction systems, however, improvement in the action to disproportionation and the selectivity can be maintained constantly for a long period of time. A similar phenomenon to the case of using the amine is also observed in the method of injecting the halogen compound as pulse. More precisely, remarkable improvement is attained in both activity to disproportionation and selectivity just after injecting the halogen compound into the reaction system. After a while, however, the activity to disproportionation is lowered to the almost same level as observed before injecting the halogen compound. The activity to isomerization is remarkably lowered just after injecting the halogen compound but is reinstated after lapse of a certain period of time. However, the activity to isomerization is finally fixed to a definite level lower than the original level observed before injecting the halogen compound. In case the halogen compound is continuously added, the above effect is relatively gradually exhibited, although its degree depends on the amount added.

Accordingly, a method wherein the amine and/or halogen compound is poured into the reaction system initially in a relatively large amount (about several % based on the weight of catalyst) at a time and then continuously in a very small amount together with the starting olefin is suited as a means for obtaining a relatively definite effect for improving the action to disproportionation and the selectivity.

For further enhancing the effect achieved by the present invention, it is especially desirable to conduct the process of the present invention jointly with other methods for improving the selectivity, for example, a method wherein an additive other than the amine and halogen compounds is added to the reaction system, a method wherein a third substance such as an alkali is added to the catalyst, and a method wherein the reaction conditions are modified, for example, by increasing the line velocity of the reactants or by varying the reaction pressure. It is a matter of course that the joint use of such methods with the process of the present invention is also involved the scope of the present invention.

The disproportionation reactions to which the process of the present invention can be applied include those of propylene and 1-butene, co-disproportionation reactions of 2-butene and isobutene and other various disproportionation and co-disproportionation reactions of other linear olefins.

The reaction temperature is preferably within a range of 350°–500° C, especially 400°–450° C. Tungsten oxide carried on a support such as silica or alumina, especially on silica gel is preferable as the supported tungsten oxide catalyst for the present invention.

The following examples are included merely to aid in the understanding of the present invention, and variations may be made by anyone skilled in the art without departing from the spirit and scope of the invention.

To clarify the influence of various kinds of compounds on the activity of the catalyst to disproportionation and isomerization, the reactions illustrated in examples given herein were conducted under such conditions that the conversion rate for disproportionation is low but the conversion rate for isomerization is high. Accordingly, the present invention is not restrained by the extents of the reaction conditions and of the conversion rates given in the examples.

In the examples, Selectivity A stands for a percentage of the disproportionation product of 1-butene (ethylene plus straight chain hexenes) to the isomerization product of 1-butene (2-butene), while Selectivity B for the percentage of the disproportionation product of 1-butene to the total disproportionation products (ethylene + propylene + straight chain pentenes and straight chain hexenes).

EXAMPLE 1

Silica gel as support having a specific surface area of 270 m$^2$/g and an apparent specific gravity of 0.37 was impregnated with an aqueous solution of ammonium tungstate, dried and baked to prepare a $WO_3$—$SiO_2$ catalyst (8 wt. % as $WO_3$). A quartz glass reaction tube was charged with 0.50 g of the catalyst and the reaction was conducted by passing 1-butene in a flow rate of 10 liters/hr. through the tube at a reaction temperature of 400° C. In general, the disproportionation reaction of olefins in the presence of a $WO_3$—$SiO_2$ catalyst usually shows an induction period. Under the reaction conditions illustrated in this example, however, the conversion rate of an olefin reaches an almost constant value after lapse of one hour. Accordingly, the result of analysis obtained for a sample isolated just one hour after initiation of the reaction is shown herein as a standard for the case of adding no ammonia. Addition of ammonia to the reaction system was commenced just after isolation of the sample. The amount of ammonia added and the progress of isolating samples with the lapse of time are shown in Table 1 below. The results of gas chromatography performed on the samples are shown in Table 2.

Table 1

| Time (hr.: min) | Addition of ammonia and results of analysis | |
|---|---|---|
| 0:00 | Introduction of 1-butene initiated | |
| 1:00 | Sample 1; | introduction of ammonia initiated ($NH_3$ 80 cc/hr) |
| 1:30 | Sample 2 | |
| 2:30 | Sample 3 | |
| 3:30 | Sample 4; | flow rate of ammonia increased ($NH_3$ 150 cc/hr) |
| 4:00 | Sample 5 | |
| 4:30 | Sample 6; | introduction of ammonia stopped |
| 5:00 | Sample 7 | |

Table 2*

| Sample No. | 1 | 2 | 3 | 4 | 5 | 6 | 7 |
|---|---|---|---|---|---|---|---|
| Amount of ammonia added (mol % based on 1-butene) | 0 | 0.8 | 0.8 | 0.8 | 1.5 | 1.5 | 0 |
| Concentration of products (mol %) | | | | | | | |
| Etylene | 0.49 | 0.57 | 1.29 | 1.39 | 1.32 | 1.40 | 0.41 |
| Propylene | 1.63 | 1.14 | 0.74 | 0.62 | 0.44 | 0.43 | 0.93 |
| 2-Butenes | 44.34 | 33.88 | 11.70 | 9.25 | 7.15 | 6.60 | 34.77 |
| Straight chain pentenes | 1.39 | 0.98 | 0.68 | 0.58 | 0.38 | 0.37 | 0.81 |
| Straight chain hexenes | 0.55 | 0.60 | 1.32 | 1.41 | 1.35 | 1.41 | 0.47 |
| Others | 0.09 | 0.05 | 0.03 | 0.03 | 0.03 | 0.03 | 0.03 |

*Catalyst $WO_3$-$SiO_2$ 0.05g; Flow rate of 1-butene 10 liters/hr; Reaction temperature 400° C These tables evidently show that addition of ammonia serves, after lapse of an induction period produced thereby, to reduce the formation of cis- and trans-2- butene which is caused by isomerization of 1-butene and, as the result, the formation of propylene and straight chain pentenes which is caused by the disproportionation reaction of 1-butene and 2-butene is reduced and that the amounts of ethylene and straight chain hexenes produced by the disproportionation reaction of 1-butene alone is significantly increased. Further, this example shows that as poisoning to the activity of the catalyst to isomerization is enhanced with the increase in the amount of ammonia added, the selectivity is also enhanced. In Table 2, "others" are branched chain $C_5$- and $C_6$-olefins and $C_7$- or higher olefins. The amount of these olefins is decreased by the addition of ammonia.

EXAMPLE 2

Using the same catalyst and reaction apparatus as described in Example 1, the reaction was carried out at 450° C. In this case, the amount of the catalyst used and the flow rate of 1-butene were 0.50 g and 10 liters/hr, respectively, as described in Example 1. At first, the reaction started on condition that no ammonia was added to the reaction system. After the lapse of one hour induction period, a part of the reaction mixture was taken out as sample and the addition of ammonia was commenced at once. In this case, the so-called induction period, i.e. a period of time required for allowing the reaction to reach to a definite rate, was also observed after addition of ammonia or after varying the amount of ammonia added. Table 3 shows the results of analysis of the product at each time the reaction was considered to reach to an almost definite rate in the cases of (a) no ammonia being added, (b) the amount of ammonia added being 80cc/hr and (c) the amount of ammonia being 200 cc/hr. As is evident from this table, an effect similar to that described in Example 1 was exhibited even in the event the reaction temperature is high and the conversion rate is relatively high.

It is evident that the conversion rate for isomerization of 1-butene is reduced down to several percents by the addition of ammonia and, as the result, the amounts of ethylene and straight chain hexenes formed are increased. It is also evident that the amounts of branched chain $C_5$- and $C_6$-olefins and $C_7$- or higher olefins are decreased with the decrease in the amounts of propylene and straight chain pentenes.

Table 3*

| Amount of ammonia added (mol % based on 1-butene) | 0 | 0.8 | 2 |
| --- | --- | --- | --- |
| Concentration of products (mol %) | | | |
| Ethylene | 5.34 | 6.74 | 6.72 |
| Propylene | 11.84 | 4.45 | 2.84 |
| 2-Butenes | 21.68 | 8.46 | 5.78 |
| Straight chain pentenes | 9.18 | 3.70 | 2.41 |
| Straight chain hexenes | 5.24 | 6.56 | 6.58 |
| Others | - | 0.90 | 0.39 |

*Reaction temperature: 450° C

EXAMPLE 3

Table 4 shows a result obtained by adding ammonia to a 1:1 (molar ratio) mixture of trans-2-butene and isobutene reacted in the presence of the same catalyst as used in Example 1. The reaction conditions adopted in this case were:

The amount of the catalyst : 2.0 g
The reaction temperature : 450° C
The flow rate of the olefins : 18 liters/hr The reaction was initiated prior to the addition of ammonia, and a sample of the reaction product was collected after the lapse of the induction period. The addition of ammonia to the reaction system was then initiated. The flow rate of ammonia was 180 cc/hr and the amount thereof corresponded to 1 mol % based on the olefins. In the table, "Ratio of disproportionation" stands for the ratio of formation of olefins other than $C_4$-olefins while "Ratio of selection for isoamylene" stands for the ratio of isoamylene to all of $C_5$-olefins formed.

The ratio of disproportionation was somewhat lowered temporarily by the addition of ammonia but was reinstated afterward and tended to increase gradually. However, it was at the same level as observed before the addition of ammonia. On the other hand, the ratio of selection for isoamylene was rapidly increased by the addition of ammonia and then continuously gradually increased with the lapse of time. The amount of higher olefins formed as by-products was found to decrease by the addition of ammonia.

Table 4

| Period of time after initiation of the reaction (hr:min) | 1:00 | 1:02 | 1:30 | 2:00 | 3:00 | 4:00 | 5:00 |
| --- | --- | --- | --- | --- | --- | --- | --- |
| Concentration of product (mol %) | | | | | | | |
| Ethylene | 1.77 | | 1.13 | 1.25 | 1.30 | 1.29 | 1.35 |
| Propylene | 13.54 | | 12.44 | 13.33 | 13.88 | 14.02 | 14.38 |
| Isoamylenes | 8.56 | | 9.48 | 10.91 | 11.85 | 11.94 | 12.40 |
| Straight chain pentenes | 3.69 | Additon of ammonia initiated | 2.22 | 2.01 | 1.85 | 1.66 | 1.55 |
| Branched chain hexenes | 1.35 | | 0.93 | 1.10 | 1.23 | 1.15 | 1.21 |
| Straight chain hexenes | 0.47 | | 0.17 | 0.14 | 0.12 | 0.09 | 0.08 |
| $C_7$ + olefins | 0.40 | | 0.17 | 0.20 | 0.18 | 0.17 | 0.15 |
| Ratio of disproportionation (%) | 29.8 | | 26.5 | 29.0 | 30.4 | 30.3 | 31.1 |
| Ratio of selection for isoamylene* (%) | 69.9 | | 81.0 | 84.4 | 86.5 | 87.3 | 88.9 |

*Ratio of selection for isoamylene $$= \left( \frac{\text{isoamylene}}{\text{isoamylene} + \text{all } C_5\text{-olefins}} \right) \times 100$$

EXAMPLE 4

Using the same catalyst and reaction conditions as described in Example 1, 1-butene was passed through the reaction tube at a flow rate of 10 liters/hr. During this reaction, 5 μ liters (about 3.7 mg) of n-butylamine was injected into the reaction tube by means of a microsyringe through silicone rubber stopper fitted to the top of the reaction tube. The results of analysis of the reaction product before and after the injection are shown in Table 5 wherein "other products" are a mixture of isoamylenes, isohexenes and $C_7$-olefins.

Table 5 shows that just after the addition of 5 μ liters of n-butylamine, increase in the amount of disproportionation reaction products is significant and a remakable improvement in the selectivity is also noted because of decrease in the amount of 2-butene which is an isomerization product of butene-1.

Table 5

| Period of time after initiation of the reaction (min.) | 60 | 90 | 95 | 100 | 120 | 150 | 180 |
|---|---|---|---|---|---|---|---|
| Concentration of product (mol %) | | | | | | | |
| Ethylene | 1.30 | 1.31 | | 2.13 | 0.98 | 0.90 | 0.91 |
| Propylene | 3.29 | 3.23 | | 4.80 | 2.61 | 2.29 | 2.25 |
| Cis-2-butene | 15.89 | 15.63 | | 13.75 | 16.83 | 16.69 | 16.46 |
| Trans-2-butene | 16.40 | 16.04 | | 14.36 | 17.45 | 17.21 | 16.84 |
| 1-Pentene | 0.27 | 0.26 | n-Butylamine | 0.39 | 0.22 | 0.19 | 0.19 |
| 2-Pentene | 2.48 | 2.43 | injected | 3.59 | 2.01 | 1.68 | 1.70 |
| 1-Hexene | 0.08 | 0.07 | | 0.11 | 0.06 | 0.05 | 0.05 |
| 2-Hexene | 0.59 | 0.58 | | 0.86 | 0.47 | 0.37 | 0.40 |
| 3-Hexene | 0.74 | 0.76 | | 1.31 | 0.38 | 0.47 | 0.52 |
| Other products | 0.14 | 0.11 | | 0.20 | 0.11 | 0.05 | 0.06 |
| Ratio of selection (%) | | | | | | | |
| A | 8.4 | 8.6 | | 15.7 | 6.1 | 5.3 | 5.6 |
| B | 31.0 | 31.5 | | 33.4 | 30.2 | 30.1 | 31.2 |

EXAMPLE 5

Table 6 shows a result obtained by injecting 5 μ liters (about 3.7 mg) of isobutylamine into 1-butene reacted in the presence of the same catalyst as used in Example 1 under the same reaction conditions as adopted in Example 1. In Table 6, the definitions for "Other products" and "Ratio of selection" are same as in Table 5. As noted in the case of using n-butylamine, a tendency to enhancing the activity to disproportionation and a tendency to lowering the activity to isomerization were also noted in the case of using isobutylamine. This effect is rather significant in the case of using isobutylamine.

Table 6

| Period of time after initiation of the reaction (min.) | 60 | 90 | 95 | 100 | 120 | 150 | 180 |
|---|---|---|---|---|---|---|---|
| Concentration of product (mol %) | | | | | | | |
| Ethylene | 1.30 | 1.20 | | 3.55 | 0.90 | 0.80 | 0.79 |
| Propylene | 3.70 | 3.47 | | 7.75 | 2.81 | 2.43 | 2.31 |
| Cis-2-butene | 17.02 | 17.23 | | 12.61 | 18.70 | 18.62 | 18.26 |
| Trans-2-butene | 17.69 | 17.86 | | 13.58 | 19.63 | 19.39 | 18.87 |
| 1-Pentene | 0.31 | 0.28 | Isobutylamine | 0.54 | 0.24 | 0.20 | 0.19 |
| 2-Pentene | 2.81 | 2.66 | injected | 4.77 | 2.15 | 1.87 | 1.79 |
| 1-Hexene | 0.08 | 0.08 | | 0.12 | 0.06 | 0.05 | 0.05 |
| 2-Hexene | 0.63 | 0.58 | | 0.98 | 0.46 | 0.40 | 0.39 |
| 3-Hexene | 0.73 | 0.70 | | 1.64 | 0.51 | 0.45 | 0.45 |
| Other products | 0.17 | 0.15 | | 0.28 | 0.15 | 0.14 | 0.10 |
| Ratio of selection (%) | | | | | | | |
| A | 7.9 | 7.3 | | 24.0 | 5.0 | 4.5 | 4.6 |
| B | 28.6 | 28.5 | | 32.5 | 27.1 | 27.4 | 28.3 |

EXAMPLE 6

Experiments were performed using the same catalyst and reaction conditions as described in Example 1 except that 5 μ liters of diethylamine, triethylamine and piperidine were respectively added to the reaction system. The results of these experiments are shown in Table 7 wherein each Sample No. 1 was extracted from the reaction product after the lapse of 90 minutes from the initiation of the reaction, i.e. 5 minutes before the injection of the relevant amine; each Sample 2 was extracted after the lapse of 100 minutes from the initiation of the reaction, i.e. 5 minutes after the injection of the relevant amine; and each Sample 3 was extracted 25 minutes after the injection of the relevant amine.

Although the effect achieved by diethylamine or triethylamine is lower than that achieved by isobutylamine, there diethylamine and triethylamine are obviously effective for enhancing the activity to disproportionation and improving the selectivity. In the case of using piperidine, not only the activity to disproportionation but also the activity to isomerization were poisoned. As the activity to isomerization is considerably poisoned, however, the use of piperidine gives as a whole a remarkable effect for improving the selectivity. Further, the poisonous effect of piperidine to the activity to disproportionation may be regarded temporary.

Table 7

| Substance added | Diethylamine | | | Triethylamine | | | Piperidine | | |
|---|---|---|---|---|---|---|---|---|---|
| Sample No. | 1 | 2 | 3 | 1 | 2 | 3 | 1 | 2 | 3 |
| Concentration of products (mol %) | | | | | | | | | |
| Ethylene | 0.88 | 1.01 | 0.71 | 0.86 | 0.92 | 0.72 | 0.94 | 0.56 | 0.97 |
| Propylene | 2.82 | 2.65 | 2.19 | 2.59 | 2.21 | 2.07 | 3.07 | 0.08 | 1.35 |
| Cis-2-butene | 19.91 | 17.66 | 19.79 | 18.29 | 16.22 | 18.18 | 19.56 | 2.13 | 11.35 |
| Trans-2-butene | 21.13 | 17.97 | 20.60 | 19.30 | 16.26 | 18.71 | 20.85 | 1.94 | 10.73 |
| 1-Pentene | 0.24 | 0.21 | 0.18 | 0.22 | 0.18 | 0.17 | 0.26 | 0.01 | 0.09 |
| 2-Pentene | 2.15 | 2.03 | 1.68 | 1.97 | 1.69 | 1.59 | 2.33 | 0.07 | 1.05 |
| 1-Hexene | 0.06 | 0.06 | 0.05 | 0.06 | 0.05 | 0.05 | 0.07 | 0.01 | 0.03 |
| 2-Hexene | 0.45 | 0.46 | 0.35 | 0.43 | 0.40 | 0.35 | 0.49 | 0.05 | 0.29 |
| 3-Hexene | 0.47 | 0.59 | 0.39 | 0.47 | 0.55 | 0.41 | 0.50 | 0.50 | 0.69 |
| Other products | 0.10 | 0.08 | 0.08 | 0.10 | 0.07 | 0.07 | 0.12 | 0.01 | 0.02 |
| Ratio of selection (%) | | | | | | | | | |
| A | 4.6 | 6.0 | 3.7 | 4.8 | 5.9 | 4.1 | 4.9 | 27.5 | 9.0 |
| B | 26.3 | 30.2 | 27.0 | 27.6 | 32.0 | 28.5 | 26.1 | 87.5 | 44.5 |

EXAMPLE 7

In an experiment using the same catalyst and the same reaction conditions as described in Example 1, isobutylamine was added to 1-butene at a flow rate of 12.5 $\mu$ liters/hr over there hours from 1 hour and 10 minutes to 4 hours and 10 minutes after the initiation of the reaction. The results of analysis of the product samples formed before, during and after the addition of isobutylamine are shown in Table 8. The amount of isobutylamine fed at a flow rate of 12.5 $\mu$ liters/hr corresponds to about 0.03 mol % based on the amount of 1-butene fed at a rate of 10 liters/hr. As shown in Table 8, the activity to disportionation and the selectivity are improved and kept almost definite even by the addition of such a very small amount of isobutylamine. Thus, it has been found that even in the case of such compound as exhibits the effect only temporarily by the pulse method, the effect can be maintained by continuously adding such compound.

the reaction tube at a flow rate of 10 liters/hr. During this reaction, 5 $\mu$ liters (about 7.5 mg) of chloroform was injected into the reaction tube by means of a microsyringe through a silicone rubber stopper fitted to the top of the reaction tube. The results of analysis of the reaction product before and after the injection are shown in Table 9 wherein "other products" are a mixture of isoamylenes, isohexenes and $C_7$-olefins.

As is shown in Table 9, increase in the amounts of ethylene and straight chain hexenes just after the injection of 5 $\mu$ liters of chloroform is indeed significant, thus showing increase in the rate of disproportionation reaction. On the other hand, the amount of 2-butenes formed is reduced to ½ or less, thus showing remarkable improvement in the selectivity. Although the enhanced activity to disproportionation is not maintained for a long period of time, the poisoned activity to isomerization is not reinstated for a long period of time. Thus, it is now evident that the addition of chloroform remarkably improves the activity and selectivity of the carried tungsten oxide catalyst to disproportionation.

Table 8

| Period of time after initiation of the reaction (hr:min) | 1:00 | 1:10 | 1:30 | 2:00 | 3:00 | 4:00 | 4:10 | 4:20 | 5:00 |
|---|---|---|---|---|---|---|---|---|---|
| Concentration of product (mol %) | | | | | | | | | |
| Ethylene | 0.72 | Injection of | 0.96 | 1.31 | 1.16 | 1.16 | Injection of | 0.57 | 0.47 |
| Propylene | 2.38 | isobutylamine | 1.36 | 1.75 | 1.35 | 1.28 | isobutylamine | 1.65 | 1.44 |
| Cis-2-butene | 18.62 | initiated | 12.56 | 12.33 | 11.59 | 11.22 | stopped | 17.92 | 18.52 |
| Trans-2-butene | 19.76 | | 12.58 | 12.24 | 11.33 | 10.87 | | 18.44 | 19.15 |
| 1-Pentene | 0.21 | | 0.12 | 0.14 | 0.11 | 0.10 | | 0.14 | 0.12 |
| 2-Pentene | 1.76 | | 1.04 | 1.33 | 1.03 | 0.97 | | 1.26 | 1.09 |
| 1-Hexene | 0.05 | | 0.05 | 0.06 | 0.05 | 0.05 | | 0.03 | 0.03 |
| 2-Hexene | 0.36 | | 0.36 | 0.47 | 0.38 | 0.37 | | 0.27 | 0.23 |
| 3-Hexene | 0.36 | | 0.61 | 0.84 | 0.76 | 0.78 | | 0.33 | 0.26 |
| Other products | 0.12 | | 0.07 | 0.08 | 0.07 | 0.06 | | 0.09 | 0.09 |
| Ratio of selection (%) | | | | | | | | | |
| A | 3.9 | | 7.9 | 10.9 | 10.3 | 10.7 | | 3.3 | 2.6 |
| B | 25.5 | | 44.0 | 45.4 | 48.6 | 50.1 | | 28.2 | 27.2 |

EXAMPLE 8

Using the same catalyst and reaction conditions as described in Example 1, 1-butene was passed through

Table 9

| Period of time after initiation of the reaction (min.) | 60 | 90 | 95 | 100 | 120 | 150 | 180 |
|---|---|---|---|---|---|---|---|
| Concentration of products (mol %) | | | | | | | |
| Ethylene | 1.01 | 1.07 | Chloroform | 2.96 | 0.84 | 0.77 | 0.74 |
| Propylene | 2.91 | 2.96 | injected | 3.43 | 1.12 | 0.95 | 0.90 |
| Cis-2-butene | 17.12 | 16.72 | | 7.61 | 10.42 | 10.27 | 10.17 |
| Trans-2-butene | 17.65 | 17.19 | | 7.40 | 9.99 | 9.84 | 9.72 |

Table 9-continued

| Period of time after initiation of the reaction (min.) | 60 | 90 | 95 | 100 | 120 | 150 | 180 |
| --- | --- | --- | --- | --- | --- | --- | --- |
| 1-Pentene | 0.24 | 0.24 |  | 0.26 | 0.08 | 0.06 | 0.06 |
| 2-Pentene | 2.22 | 2.25 |  | 2.55 | 0.87 | 0.75 | 0.70 |
| 1-Hexene | 0.70 | 0.07 |  | 0.08 | 0.03 | 0.03 | 0.02 |
| 2-Hexene | 0.49 | 0.50 |  | 0.67 | 0.24 | 0.21 | 0.26 |
| 3-Hexene | 0.57 | 0.62 |  | 2.07 | 0.62 | 0.57 | 0.55 |
| Other products | 0.11 | 0.11 |  | 0.15 | 0.04 | 0.01 | 0.02 |
| Ratio of selection (%) |  |  |  |  |  |  |  |
| A | 6.2 | 6.7 |  | 38.5 | 8.5 | 7.9 | 7.6 |
| B | 28.5 | 29.3 |  | 48.1 | 45.5 | 47.3 | 47.6 |

EXAMPLE 9

Table 10 shows a result obtained by injecting 5 μ liters (about 8 mg) of carbon tetrachloride into 1-butene reacted in the presence of the same catalyst as used in Example 1 under the same reaction conditions as adopted in Example 1. In Table 10, the meaning of "other products" is same as in Table 9. As noted in the case of using chloroform, a tendency to increasing the conversion ratio to the disproportionation reaction and a tendency to poisoning the activity to isomerization while improving the selectivity were also noted in the case of using carbon tetrachloride. As compared with the case of using chloroform, this effect is rather strong in the case of using carbon tetrachloride.

rate of 12.5μ liters/hr. over 3 hours from 1 hour and 10 minutes to 4 hours and 10 minutes after the initiation of the reaction. The results of analysis of the reaction products formed before, during and after the addition of carbon tetrachloride are shown in Table 11. The amount of carbon tetrachloride (liquid) fed at a rate of 12.5 μ liters/hr corresponds to about 0.03 mol % based on the amount of 1-butene (gas) fed at a rate of 10 liters/hr. As shown in Table 11, the activity to disproportionation and the selectivity are gradually improved and, after 2 or 3 hours, this influence is shown by extremely high values, even by the addition of such a very small amount of carbon dioxide tetrachloride. Furthermore, the conversion ratio to disproportionation and the ratio of selection are enhanced just after stopping Table 10

| Period of time after initiation of the reaction (min.) | 60 | 90 | 95 | 100 | 120 | 150 | 180 |
| --- | --- | --- | --- | --- | --- | --- | --- |
| Concentration of products (mol %) |  |  |  |  |  |  |  |
| Ethylene | 1.39 | 1.38 | Carbon | 6.68 | 1.88 | 1.18 | 0.99 |
| Propylene | 3.81 | 3.79 | tetra- | 5.18 | 2.49 | 1.44 | 1.14 |
| Cis-2-butene | 16.38 | 16.50 | chloride | 5.67 | 9.41 | 10.29 | 10.00 |
| Trans-2-butene | 17.04 | 17.20 | injected | 5.70 | 9.30 | 9.98 | 9.64 |
| 1-Pentene | 0.31 | 0.32 |  | 0.54 | 0.17 | 0.10 | 0.08 |
| 2-Pentene | 2.82 | 2.84 |  | 3.64 | 1.90 | 1.12 | 0.88 |
| 1-Hexene | 0.08 | 0.09 |  | 0.16 | 0.06 | 0.04 | 0.03 |
| 2-Hexene | 0.64 | 0.64 |  | 1.20 | 0.50 | 0.33 | 0.27 |
| 3-Hexene | 0.75 | 0.77 |  | 4.42 | 1.41 | 0.85 | 0.72 |
| Other products | 0.14 | 0.13 |  | 0.33 | 0.10 | 0.07 | 0.03 |
| Ratio of selection (%) |  |  |  |  |  |  |  |
| A | 8.6 | 8.5 |  | 109.6 | 20.8 | 11.8 | 10.2 |
| B | 29.2 | 29.3 |  | 57.1 | 45.8 | 47.4 | 48.9 |

EXAMPLE 10

In an experiment using the same catalyst and the same reaction conditions as described in Example 1, carbon tetrachloride was added to 1-butene at a flow the injection of carbon tetrachloride. Such enhancement of the activity with the lapse of time is a character of the method of continuously adding the halogen compound.

Table 11

| Period of time after initiation of the reaction (hr: min.) | 1:00 | 1:10 | 1:30 | 2:00 | 3:00 | 4:00 | 4:10 | 4:30 | 5:00 |
| --- | --- | --- | --- | --- | --- | --- | --- | --- | --- |
| Concentration of products (mol %) |  |  |  |  |  |  |  |  |  |
| Ethylene | 1.05 | Injection | 1.40 | 2.31 | 3.51 | 4.51 | Injection | 7.06 | 2.17 |
| Propylene | 3.24 | of carbon | 2.47 | 3.45 | 4.42 | 4.84 | of carbon | 6.32 | 2.56 |
| Cis-2-butene | 17.89 | tetra- | 12.48 | 9.18 | 6.66 | 5.08 | tetra- | 3.50 | 7.31 |
| Trans-2-butene | 18.91 | chloride | 12.87 | 9.43 | 6.86 | 5.26 | chloride | 3.63 | 7.11 |
| 1-Pentene | 0.28 | initiated | 0.21 | 0.28 | 0.40 | 0.47 | stopped | 0.56 | 0.17 |
| 2-Pentene | 2.44 |  | 1.85 | 2.52 | 3.21 | 3.49 |  | 4.60 | 1.93 |
| 1-Hexene | 0.07 |  | 0.08 | 0.10 | 0.12 | 0.13 |  | 0.12 | 0.06 |
| 2-Hexene | 0.53 |  | 0.56 | 0.74 | 0.90 | 0.93 |  | 0.73 | 0.47 |
| 3-Hexene | 0.56 |  | 0.84 | 1.48 | 2.46 | 3.37 |  | 6.19 | 1.75 |
| Other products | 0.14 |  | 0.13 | 0.21 | 0.29 | 0.35 |  | 0.45 | 0.13 |
| Ratio of selection |  |  |  |  |  |  |  |  |  |

Table 11-continued

| Period of time after initiation of the reaction (hr: min.) | 1:00 | 1:10 | 1:30 | 2:00 | 3:00 | 4:00 | 4:10 | 4:30 | 5:00 |
|---|---|---|---|---|---|---|---|---|---|
| A | 6.0 |  | 11.4 | 24.9 | 51.7 | 86.5 |  | 197.8 | 30.9 |
| B | 27.1 |  | 38.9 | 42.6 | 46.5 | 50.4 |  | 65.8 | 48.8 |

EXAMPLE 11

At the time of initiating the addition of carbon tetrachloride under the same reaction conditions as described in Example 10, 10μ liters of carbon tetrachloride was injected and successively additional carbon tetrachloride was added continuously at a flow rate of 12.5 μ liters/hr. A result of this experiment is shown in Table 12. In the case of this experiment, the activity to disproportionation and the selectivity are significantly enhanced just after the addition of carbon tetrachloride. Although variations with the lapse of time still remain, it is possible to conduct the highly selective reaction in a stable state. As in the case of Example 10, a temporary enhancement is observed in the activity to disproportionation and in the selectivity just after stopping the addition of carbon tetrachloride.

Table 12

| Period of time after initiation of the reaction (hr: min.) | 1:00 | 1:10 | 1:20 | 2:00 | 3:00 | 4:00 | 4:10 | 4:20 | 5:00 |
|---|---|---|---|---|---|---|---|---|---|
| Concentration of products (mol %) |  |  |  |  |  |  |  |  |  |
| Ethylene | 0.85 | Injection | 3.42 | 3.88 | 4.68 | 5.37 | Injection | 10.56 | 1.64 |
| Propylene | 2.80 | of carbon | 4.36 | 4.49 | 4.78 | 5.00 | of carbon | 7.50 | 1.79 |
| Cis-2-butene | 19.32 | tetra- | 7.62 | 6.28 | 5.00 | 4.25 | tetra- | 2.24 | 7.46 |
| Trans-2-butene | 20.48 | chloride | 7.77 | 6.40 | 5.14 | 4.40 | chloride | 2.45 | 7.12 |
| 1-Pentene | 0.25 | initiated | 0.37 | 0.40 | 0.44 | 0.47 | stopped | 0.76 | 0.11 |
| 2-Pentene | 2.11 |  | 3.12 | 3.24 | 3.45 | 3.54 |  | 5.34 | 1.35 |
| 1-Hexene | 0.06 |  | 0.12 | 0.12 | 0.13 | 0.12 |  | 0.13 | 0.04 |
| 2-Hexene | 0.44 |  | 0.89 | 0.88 | 0.86 | 0.84 |  | 0.74 | 0.35 |
| 3-Hexene | 0.44 |  | 2.29 | 2.83 | 3.54 | 4.04 |  | 9.06 | 1.29 |
| Other products | 0.13 |  | 0.29 | 0.30 | 0.35 | 0.36 |  | 0.60 | 0.08 |
| Ratio of selection |  |  |  |  |  |  |  |  |  |
| A | 4.5 | 43.7 | 60.8 | 90.8 | 119.9 |  | 437 | 22.8 |  |
| B | 25.8 |  | 46.1 | 51.5 | 51.5 | 53.3 |  | 60.1 | 50.5 |

What is claimed is:

1. A process for the selective disproportionation reaction of olefins which comprises heating an olefin in a reaction zone to disproportionation temperature in the presence of a supported tunsten oxide catalyst and of an initial amount of at least one halogen compound and as the disproportionation reaction continues, introducing additional amounts of such halogen compound at least intermittently, said halogen compound being selected from the group consisting of chloroform, carbon tetrachloride, dibromomethane, 1,1-dibromoethane and butyl bromide.

2. A process according to claim 1 wherein such halogen compound is present in an amount of 0.001–5 mol % based on the starting olefin.

3. A process according to claim 1 wherein said olefin is propylene, 1-butene and a mixture of 2-butene and isobutene.

4. A process according to claim 1 wherein said disproportionation temperature is within the range of about 350°–500° C.

5. The process of claim 1 wherein fresh olefin is delivered continuously into contact with said catalyst and the reaction products withdrawn continuously therefrom and said additional halogen compound is introduced continuously in admixture with said olefin.

6. A process for the selective disproportionation reaction of olefins which comprises heating an olefin in a reaction zone to disproportionation temperature in the presence of a supported tungsten oxide catalyst and of an initial amount of at least one amine compound and as the disproportionation reaction continues, introducing additional amounts of said amine compound at least intermittently, said amine compound being selected from the group consisting of ammonia, n-butylamine, isobutylamine, diethylamine, triethylamine and piperidine.

7. A process according to claim 6 wherein such amine compound is present in an amount of 0.001–5 mol % based on the starting olefin.

8. A process according to claim 6 wherein said olefin is propylene, 1-butene and a mixture of 2-butene and isobutene.

9. A process according to claim 6 wherein said disproportionation temperature is within the range of about 350°–500° C.

10. The process of claim 6 wherein fresh olefin is delivered continuously into contact with said catalyst and the reaction products withdrawn continuously therefrom and said additional amine compound is introduced continuously in admixture with said olefin.

* * * * *